United States Patent
Nappa et al.

(10) Patent No.: US 6,207,869 B1
(45) Date of Patent: *Mar. 27, 2001

(54) PROCESS FOR PERHALOFLUORINATED BUTANES AND HEXANES

(75) Inventors: Mario Joseph Nappa, Newark, DE (US); Allen Capron Sievert, Elkton, MD (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/519,791

(22) Filed: Mar. 7, 2000

Related U.S. Application Data

(62) Division of application No. 08/738,117, filed on Oct. 25, 1996, now Pat. No. 6,066,768, which is a continuation of application No. 08/166,432, filed on Dec. 14, 1993, now abandoned.

(51) Int. Cl.$^7$ ................................................. C07C 19/08
(52) U.S. Cl. ............................................................... 570/134
(58) Field of Search ..................................... 570/134, 137

(56) References Cited

U.S. PATENT DOCUMENTS

| | | | | |
|---|---|---|---|---|
| 4,954,666 | * | 9/1990 | Bielefeldt et al. .................... | 570/132 |
| 6,066,768 | * | 5/2000 | Nappa et al. ......................... | 570/134 |

* cited by examiner

Primary Examiner—Alan Siegel
(74) Attorney, Agent, or Firm—James E. Shipley

(57) ABSTRACT

The instant invention relates to producing perhalofluorobutanes and perhalofluorohexanes, more particularly it relates to their production by utilizing tetrafluoroethylene (hereinafter referred to as "TFE") and chlorotrifluoroethylene (hereinafter referred to as "CTFE") with selected perhalofluoroethanes containing 2 to 4 nonfluorine halogen and 2 to 4 fluorine substituents in the presence of a polyvalent metal halide such as an aluminum chloride or chlorofluoride as catalyst.

3 Claims, No Drawings

PROCESS FOR PERHALOFLUORINATED BUTANES AND HEXANES

This is a division of application Ser. No. 08/738,117 filed Oct. 25, 1996, now U.S. Pat. No. 6,066,768, which in turn is a continuation of application Ser. No. 08/166,432 filed Dec. 14, 1993, now abandoned.

FIELD OF THE INVENTION

This is a division of application Ser. No. 08/738,117 filed Oct. 25, 1996, which in turn is a continuation of Ser. No. 08/166,432 filed Dec. 14, 1993. The instant invention relates to producing perhalofluorobutanes and perhalofluorohexanes, more particularly it relates to their production by utilizing tetrafluoroethylene (hereinafter referred to as "TFE") and chlorotrifluoroethylene (hereinafter referred to as "CTFE") with selected perhalofluoroethanes containing 2 to 4 nonfluorine halogen substiutuents, and 2 to 4 fluorine substituents in the presence of a polyvalent metal halide such as an aluminum chloride or chlorofluoride as catalyst.

The perhalofluoroalkanes can be used as intermediates for the manufacture of hydrofluorobutanes which in turn in view of their inherently low ozone depletion potentials, are environmentally attractive alternatives for perchlorofluorocarbons (CFC's) in such established uses as refrigerants, expansion agents for making foams, aerosols, heat transfer media, propellants, solvents, cleaning and drying agents, gaseous dielectrics, power cycle working fluids, polymerization media, carrier fluids, fire extinguishants, among other applications.

BACKGROUND OF THE INVENTION

Joyce, U.S. Pat. No. 2,462,402 (Feb. 22, 1949) discloses a process for the production of highly halogenated fluoroalkanes which comprises contacting TFE with a polyhalogenated alkane, preferably a methane, containing at least one chlorine atom and no more than two fluorine atoms, in the presence of a polyvalent metal halide catalyst, preferably aluminum chloride.

Sievert, et. al., in U.S. Pat. No. 5,157,171 (Oct. 20, 1992) disclose a process for preparing chlorofluorinated propanes, CHCl2F5, by contacting monofluorodichloromethane (CHCl2F) with TFE in the presence of a modified aluminum chloride catalyst containing fluoride as well as chloride ligands.

The disclosure of the previously identified references is hereby incorporated by reference.

SUMMARY OF THE INVENTION

One aspect of the invention relates to a process for producing valuable perhalofluorobutanes from commercially available perhalofluoroethanes and polyfluoroethylenes such as tetrafluoroethylene (TFE) and chlorotrifluoroethylene (CTFE).

The inventive process relates to producing perhalofluorobutanes, where "halo" represents non-fluoro halogens, in particular Cl and/or Br, by reacting TFE and/or CTFE with one or more selected perhalofluoroethanes.

Broadly, the invention comprises:
(i) contacting
 (a) CYF=CF$_2$, where Y is Cl or F, with
 (b) a perhalofluoroethane selected from the group comprising CX$_2$FCX$_2$F or CX$_2$FCXF$_2$ or CF$_3$CX$_2$F or CBrF$_2$CF$_{2x}$ where X can be either Cl or Br, in the presence of (c) a catalytically effective polyvalent metal halide, preferably aluminum chloride or aluminum chlorofluoride, at a temperature and pressure and for a time effective to produce
(d) a reaction product mixture containing at least one perhalofluorobutane selected from the group comprising C$_4$YX$_4$F$_5$, C$_4$YX$_3$F$_6$, C$_4$BrYXF$_7$, and C$_4$YX$_2$F$_7$ where Y and X are as defined above; and
(ii) recovering at least one of said perhalofluorobutanes from the reaction mixture.

The inventive process is capable of producing perhalofluorobutanes having the formula C4X2-5F5-8, X=Br or Cl, derived from perhalofluoroethanes as defined above by reaction with TFE that may be represented by the following equations (1)–(3):

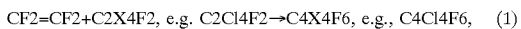

CF2=CF2+C2X4F2, e.g. C2Cl4F2→C4X4F6, e.g., C4Cl4F6,  (1)

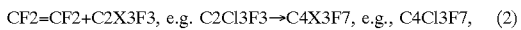

CF2=CF2+C2X3F3, e.g. C2Cl3F3→C4X3F7, e.g., C4Cl3F7,  (2)

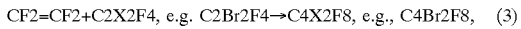

CF2=CF2+C2X2F4, e.g. C2Br2F4→C4X2F8, e.g., C4Br2F8,  (3)

wherein usually the fluorine content of each of the products C4X4F6, C4X3F7, and C4X2F8 is the sum of the fluorine contents of the low and perhalofluoroethane reactants.

Similarly, the inventive process is capable of producing perhalofluorobutanes having the formula C4X2-5F5-8, X=Br or Cl, derived from perhalofluoroethanes as defined above by reaction with CTFE that may be represented by the following equations (4)–(6):

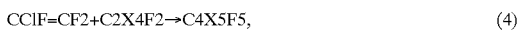

CClF=CF2+C2X4F2→C4X5F5,  (4)

CClF=CF2+C2X3F3→C4X4F6  (5)

CClF=CF2+C2X2F4→C4X3F7  (6)

wherein usually the fluorine content of each of the products C4X5F5, C4X4F6, and C4X3F7 is the sum of the fluorine contents of the CTFE and perhalofluoroethane reactants.

The reaction product mixture may contain products having fluorine content greater than the sum of the fluorine content of the starting materials. For example, the reaction of CCl2FCClF2 with TFE may yield in addition to C4Cl3F7, a C4Cl2F8 product, e.g., CF3CCl2CF2CF3. In some cases, a halogen exchange reaction may occur between the primary C4Cl3F7 product and the metal halide catalyst which contains fluorine ligands, either originally present or formed therein during the course of the reaction with a chlorofluoroethane reactant.

The reaction product mixture may also contain products having fewer fluorine groups than the sum of the fluorine groups in the starting materials. All such products with fluorine content greater or smaller than the sum of the fluorine content of the starting materials are also valuable products as they are also reducible to hydrogen containing products using known techniques, e.g., converting at least one carbon-nonfluorine halogen bond to a carbon-hydrogen bond.

When using starting materials corresponding to CX2FCX2F, where X can be Cl and/or Br, the reaction product mixture may additionally contain products derived from reaction of at least two moles of fluoroolefin with one of the perhalofluoroethane. For example, C6Cl4F10 (C2F5CCl2CCl2C2F5) and C5CCl5F9 (CClF2CF2CCl2CCl2C2F5), may both originate from TFE and CCl2FCCl2F in the presence of an aluminum chloride or chlorofluoride catalyst. Without wishing to be bound by any theory or explanation, it is believed that the nonafluoride, e.g., C5Cl5F9, may result from a halogen exchange reaction of the intermediate C4Cl4F6, or first formed product C6Cl4F10, with the aluminum chloride catalyst. The halogen exchange reaction can be shown by the following equation (7);

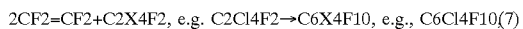
2CF2=CF2+C2X4F2, e.g. C2Cl4F2→C6X4F10, e.g., C6Cl4F10(7)

DETAILED DESCRIPTION

In accordance with the present invention perhaloftuorobutanes, as defined above and generally as the major reaction products, can be prepared by reacting TFE or CTFE with selected perhalofluoroethanes in the presence of an effective metal halide such as aluminum chloride or chlorofluoride, as catalyst.

Such reactions illustrated by equations (1)–(6) above, indicate a stoichiometry of 1 mole of the fluoroolefin per mole of the perhalofluoroethane reactant. The reaction illustrated by equation (7) indicates a stoichimetry of 2 moles of fluoroolefin per mole of reactant. Generally, however, the mole ratio of starting materials or reactants may vary from about 0.3 to about 3.0 moles of the fluoroolefin per mole of the halofluoroethane reactant with about 1:1 being used typically for making perhalofluorobutanes, whereas 2:1 being used typically for making perhalofluorohexanes.

The catalyst is typically an anhydrous aluminum chloride or chlorofluoride wherein the fluorine content ranges from about 3 to 64% by weight, and is such that the composition corresponds to that of AlCl3-rFr wherein r is typically about 1 to about 2.8 (hereinafter referred to as a "modified aluminum chloride catalyst"). Such modified aluminum chloride catalytic compositions may be prepared by reacting anhydrous AlCl3 with an excess of at least one of chlorofluorocarbon, hydrochlorofluorocarbon, or hydrofluorocarbon as disclosed in Sievert, et. al. U.S. Pat. No. 5,157,171, the disclosure of which is incorporated herein by reference. It is, however, desirable to avoid formation of AlF3 because such a composition is not believed to be an active catalyst for the instant invention.

The quantity of modified aluminum chloride used in the present process may vary widely, but usually amounts to about 1 to about 20 mole percent based on the quantity of the perhalofluoroethane.

The inventive process can be conducted batchwise, or in a continuous manner. In the continuous mode, a mixture of perhalofluoroethane and fluoroolefin can be passed through or over a bed or body of the catalyst which may be under agitation at a suitable temperature and pressure to form a product stream, and the desired products are recovered from the stream. Such recovery can be performed by using conventional methods, e.g., fractional distillation.

In the batch process, the reactants and catalyst may be combined in a suitable reactor to form a reaction mixture and the mixture held, normally under agitation, at a suitable temperature and pressure, until a desired degree of conversion to the desired perhalofluorobutanes are attained. In one embodiment, the reactor is initially charged with the catalyst, optionally in the presence of a diluent, then the perhalofluoroethane and the fluoroolefin, as separate streams or as a combined streams, in a desired mole ratio, are fed into the reactor at a controlled rate and maintained therein until the reaction is complete. If the reactor is fed with perhalofluoroethane and catalyst in the substantial absence of fluoroolefin, the system (reactor and ingredients) should be kept relatively cold, e.g., between −78 C and 10 C, to minimize reaction of the perhalofluoroethane with the catalyst, e.g., a halogen exchange reaction, or disproportionation to higher or lower perhalofluoroethanes.

The inventive process may be practiced with or without a solvent or reaction diluent. Such solvent or diluent, if used, must be substantially inert to the reactants and catalyst, and also should boil at a temperature that enables separation of the diluent from the reaction products. Representative of such diluents can be at least one of CCl4, CF3CHCl2, CCl3CF3, CF3CCl2CF3, the perhalofluorobutane products of the present inventive process, e.g., CClF2CCl2C2F5, CF3CBr2C2F5, CF3CCl2C2F5, isomers thereof, among others.

The reaction temperature may be varied, and normally is in the range of from about 0 C to about 150 C; typically in the range of from about 20 C to about 110 C.

The reaction pressure likewise may vary widely from subatmospheric to superatmospheric, but typically the reaction is carried out at somewhat elevated pressures, particularly at pressures generated autogenously in conformity with the reaction temperature employed. The pressure may be controlled by adjusting the amount of unreacted perhalofluoroethane and fluoroolefin.

The reaction time, or time necessary for substantially complete reaction, can be dependent on the temperature chosen for the reaction; generally the higher the temperature the shorter the reaction time. The completion of the reaction, however, can be determined by the change in the autogenous pressure in the reaction vessel, because the pressure drops as the reaction proceeds, so that the time at which the pressure stops decreasing can be taken as the end of the reaction period. Generally, the reaction time ranges of from about 0.25 h to about 6.0 hours. The reaction time can vary with the volume of the reactor and/or quantity of reactants.

The products of the reaction may be recovered from the reactor by conventional means such as filtration, distillation, among other conventional means. It is usually convenient to decompose the catalyst by treatment with water, and then recover the desirable reaction product by distillation.

The perhalofluoroethane starting materials for the process of this invention are selected from one or more of CCl2FCCl2F, CClF2CCl2F, CCl2FCF3, CBr2FCF3, CBrClFCF3, CBrF2CBrF2, and CBrF2CClF2. The fluoroolefin starting materials for the process of this invention are selected from one or more of CTFE (CClF=CF2) and TFE (CF2=CF2). The combination of these perhalofluoroethane starting materials with these fluoroolefin starting materials in the presence of aluminum chloride or modified aluminum chloride catalyst affords perhalofluoroalkane reaction products selected from one or more of C4Cl5F5 isomers including C2Cl5C2F5; C4Cl4F6 isomers including CClF2CCl2CF2CClF2 and CClF2CCl2CClFCF3; C4Cl3F7 isomers including CClF2CCl2C2F5; CF3CCl2CF2CClF2, and CF3CCl2CClFCF3; C4Cl2F8 isomers including CF3CCl2C2F5; C4BrClF8 isomers including CF3CBrClC2F5; C4Br2C2F5 isomers including CF3CBr2C2F5; C6Cl5F9 isomers including CClF2CF2CCl2CCl2C2F5; and C6Cl4F10 isomers including C2F5CCl2CCl2C2F5.

The following perhalofluoroalkanes reaction products are new compositions of matter:

C2Cl5C2F5, CF3CCl2CF2CClF2, CF3CBrClC2F5, CF3CBr2C2F5, CClF2CF2CCl2CCl2C2F5, and C2F5CCl2CCl2C2F5.

All of the above perhalofluoroalkanes can be used for making hydrofluorocarbons (HFCs) such as hydrofluoroalkanes, e.g., at least one of hydrofluorobutanes and hydrofluorohexames.

If desired, the perhaloproducts of the inventive process may be hydrodehalogenated to hydro-derivatives comprising at least one hydrogen substituent and correspondingly one less nonfluorohalogen substituent than present in the starting perhalofluorocarbon by being treated with one or more reducing means. Examples of suitable reducing means comprise least one of photochemical, chemical, and normally catalytic hydrogenation means. Catalytic hydrogenation may generally be effected with molecular hydrogen over a suitable catalyst, typically a Group VIII metal, as disclosed, for example, in Smith, U.S. Pat. No. 2,942,036 and Rao, U.S. Pat. No. 5,136,113; the entire disclosures of which are incorporated herein by reference.

Catalytic hydrogenation can be practiced in the liquid or vapor phase. Normally, the vapor phase is employed with a catalytic metal such as palladium that can be supported on carbon or alumina. Catalytic hydrogenation may generally be effected with molecular hydrogen over a suitable catalyst, typically a Group VIII metal, as disclosed, for example, in Smith, U.S. Pat. No. 2,942,036 and Rao, U.S. Pat. No. 5,136,113 which disclosures are incorporated herein by reference.

Hydrogenation can also be conducted in the vapor phase with a catalytic metal such as nickel, palladium, platinum, rhodium or iridium, among others. The catalytic metal is normally supported on a suitable carrier such as carbon or alumina.

The hydrodehalogenation reactions of the present invention may be conducted at temperatures between about 25 C and 250 C, normally between about 50 C and 200 C, and typically between about 100 C and 200 C. The choice of optimum hydrodehalogenation temperature will be dictated by whether the halogen being removed or replaced is chlorine or bromine, the desired degree of conversion of the perhalofluoroalkane starting material, the percent loading of the active metal upon the support, among other factors. Perbromofluoroalkanes are more readily hydrodehalogenated than are perchlorofluoroalkanes.

The hydrodehalogenation reactions may be operated at pressures between atmospheric and 100 psig or higher. The choice of pressure may be dictated by the vapor pressure of the reactants, intermediates, and products.

The ratio of hydrogen to perhalofluoroalkane employed in the dehydrohalogenation reaction may vary from about 0.5 to about 10 on a molar basis, and usually should be from about 1 to 4. Relatively large excesses of hydrogen can be employed. A deficiency of hydrogen may be used to control the conversion rate of the perhalofluoroalkane if desired.

Chemical reducing means may also include reduction with zinc in the presence of an alcohol as disclosed, for example, by Morikawa, et. al., in International Patent Application 90/08753 and by Krespan in U.S. Pat. No. 4,935,558; reduction with complex metal hydrides as disclosed by Clayton in European Patent Application 0 508,631; reduction with hydrogen iodide or with H2 in the presence of iodine or hydrogen iodide as disclosed by Anton in U.S. Pat. No. 5,208,396; the entire disclosure of these patent documents is hereby incorporated by reference.

Photochemical means include reaction of the perhalocompound with alcohols in the presence of ultraviolet light as disclosed by Posta, et. al., in Czechoslovak Patent 136,735.

Hydrofluoroalkanes produced by hydrodehalogenation of the perhalofluoroalkanes listed above include those selected from one or more of C4H5F5 isomers including C2H5C2F5 and CHF2CH2CH2CF3; C4H4F6 isomers including CHF2CH2CF2CHF2, CHF2CH2CHFCF3, and CF3CH2CH2CF3; C4H3F7 isomers including CHF2CH2C2F5; CF3CH2CF2CHF2, and CF3CH2CHFCF3; C4H2F8 isomers including CF3CH2C2F5; C6HSF9 isomers including CHF2CF2CH2CH2C2F5; C6H4F10 isomers including C2F5CH2CH2C2F5.

The following hydrofluoroalkanes hydrodehalogenation products are new compositions of matter: CHF2CH2CH2CF3, CHF2CH2CHFCF3, CHF2CH2C2F5, CHF2CF2CH2CH2C2F5. All of the hydrogenated alkanes can be used in the manner described above in connection with HFCs such as a refrigerant, cleaning and blowing agents, among other applications.

The various embodiments of this invention may be more readily understood by consideration of the following examples which are being provided to illustrate not further limit that scope of the invention.

Examples 1 to 7 exemplify the reaction of TEE with CCl2CCl2F, CCl2FCClF2, CCl2FCF3, CBrF2ClF2, CBrF2CBrF2, and CBr2FCF3.

Examples 8 and 9 exemplify the reaction of CltE with CCl2FCClF2 and CCl2FCF3.

Example 10 illustrates the hydrodebromination of CF3CBr2CF2CF3 to CF3CH2CF2CF3.

Analyses of reaction products, generally mixtures, were carried out using standard GC/GC-MS and 19F NMR methods, the abbreviations GC, GC-MS, and NMR standing for gas chromatography, gas chromatography-mass spectrometry, and nuclear magnetic resonance spectroscopy. Results are presented in GC area percents unless otherwise indicated with amounts less than about 1% to generally omitted.

EXAMPLE 1

Reaction of CCl2FCCl2F with TEE

A 400 mL "Hastelloy" C. shaker tube was charged with 3 g of CCl3F-modified aluminum chloride, 30 g (0.15 mole) of CCl2FCCl2F, and 30 g of CHCl2CF3 as a diluent. The reactor was sealed, cooled to −78 C, evacuated, and purged with nitrogen three times. The reactor was then placed in the autoclave, agitated, charged with 11 g (0.11 mole) of TEE, and heated to 42 C over the course of 45 minutes (pressure reached 101 psig). An additional 14 g (0.25 mole total) of TFE were added over the course of 1 h at a temperature of 38–49 C; uptake of TFE was obvious from the drop in pressure after each addition of TFE. Agitation and heating were stopped after an additional 6 h (final pressure 46 psig at 40 C). The product consisted of clear supernatant over a flocculent brown solid (total weight 79.5 g). Analysis of the product by GC and GC-MS indicated the following major products:

| Component | GC Area % |
| --- | --- |
| C4F8 | 0.09 |
| C2C12F2 | 0.1 |
| CHCl2CF3 | 31.3 |
| CCl3CF3 | 0.2 |
| C2F5CCl2C2F5 | 0.05 |
| CCl3C2F5 | 0.1 |
| C6Cl2F10 | 0.05 |

-continued

| Component | GC Area % |
|---|---|
| C4Cl2F6 | 0.9 |
| CCl3CCl F2 | 2.9 |
| CCl2=CCl2 | 0.09 |
| CClF2CCl2CF2CClF2 | 14.5 |
| C2F5CCl2CCl2C2F5 | 46.2 |
| CCl3CCl2CF2CF3 | 0.3 |
| CClF2CF2CCl2CCl2C2F5 | 1.3 |

Products CClF2CCl2CF3CF3 (C4Cl4F6) and CCl3CCl2CF2CF3(C4Cl5F5) are evidently formed by condensation of one mole of TEE with CCl2FCCl2F, with C4Cl5F5 being the result of halogen exchange between C4Cl4F6 and the aluminum halide catalyst. The C6Cl4F10 and C6Cl5F9 products evidently derive from two moles of lob condensing with CCl2FCCl2F, with C6ClSF9 also a product of halogen exchange between C6Cl4F10 and the aluminum halide catalyst.

The modified aluminum chloride catalyst of Example 1 was prepared as follows:

A 1 L four neck round bottom flask was charged with 150 g of aluminum chloride (AlCl3) in a dry box. The flask was passed out of the dry box and fitted with an addition funnel, a mechanical stirrer, a thermocouple, and a dry ice condenser connected to a nitrogen bubbler. The addition funnel was charged with about 525 g of CCl3F and the condenser was filled with a methanol/dry ice mixture. The CCl3F was added to the flask over the course of about 3.5 h. After the addition was complete, the mixture was stirred for 1 h and then volatiles were removed in vacuum. The resulting solid was dried under dynamic vacuum. Analysis: weight % Al=33.4; weight % F=44.7. The fluorine analysis data suggests the composition of the catalyst is approximately AlCl0.6F2.3.

EXAMPLE 2

Reaction of CCl2FCClF2 with TFE

A 400 mL "Hastelloy" C shaker tube was charged with 3 g of CCl3F-modified aluminum chloride. The reactor was sealed, cooled to −78 C, evacuated, purged with nitrogen three times, and charged with 60 g (0.32 mole) of CCl2FCClF2. The reactor was then placed in the autoclave, agitated, charged with 11 g (0.11 mole) of TFE, and heated to 31 C over the course of 45 minutes (pressure reached 5 psig). An additional 16 g (0.27 mole total) of TFE were added over the course of 1.5 h and the temperature was increased to 38 C (69 psig). Agitation and heating were stopped after an additional 4 h (final pressure 38 psig at 39 C). The product consisted of clear supernatant over a yellow solid (total weight 74.2 g). Analysis of the product by GC, GC-MS, and 19F NMR indicated the following major products in the Table below.

| Component | GC Area % | Mole % |
|---|---|---|
| CF2=CF2 | 0.3 | — |
| C4F8 | 0.1 | — |
| C6F12 | 0.3 | — |
| C8F16 | 0.07 | — |
| C6ClF11 (3 isomers) | 0.4 | — |
| CF3CCl2C2F5 | 3.8 | 3.3 |

-continued

| Component | GC Area % | Mole % |
|---|---|---|
| CCl3CF3 | 26.0 | 35.6 |
| C6Cl2F10 (2 isomers) | 0.3 | — |
| CClF2CCl2C2F5 | 57.2 | 48.8 |
| CClF2CF2CCl2CF3 | * | 2.4 |
| CF3CClFCCl2CF3 | * | 1.5 |
| C4Cl4F6 | 6.6+ | 4.4** |
| C4Cl5F5 | 3.4+ | 40** |

+Determined by GC-MS
**Structure indicated by 19F NMR

The modified aluminum chloride catalyst of Example 2 was prepared as follows:

A 500 mL three neck round bottom flask containing a PTFE-coated stirring bar was charged with 50 g of aluminum chloride (AlCl3) in a dry box. The flask was passed out of the dry box and fitted with an addition funnel and a dry ice condenser connected to a nitrogen bubbler. The addition funnel was charged with 175 mL of CCl3F and the condenser was filled with a methanol/dry ice mixture. The CCl3F was gradually added to the flask and the mixture began to reflux vigorously. The reaction continued to reflux for a hour after all of the CCl3F had been added. The reaction was not heated. Volatiles were removed in vacuum. The resulting solid was dried under dynamic vacuum to afford 35 g of off-white powder. Analysis: weight % F=47.7; weight % Al=26.6; this corresponds to a composition that is approximately AlClF2.

EXAMPLE 3

Reaction of CCl2FCF3 with TEE

A 400 mL "Hastelloy" C shaker tube was charged with 6 g of CCl3F-modified aluminum chloride. The reactor was sealed, cooled to −78 C, evacuated, purged with nitrogen three times, and charged with 80 g (0.47 mole) of CCl2FCF3. The reactor was then placed in the autoclave, agitated, charged with 10 g (0.10 mole) of TEE, and heated to 60 C over the course of 20 minutes (pressure reached 50 psig). An additional 30 g (0.40 mole total) of bled were added over the course of 0.5 h as the pressure rose to 162 psig. Agitation and heating were stopped after an additional 6 h (final pressure 127 psig at 60 C). The product consisted of clear supernatant over a flocculent brown solid (total weight 93.2 g); after filtration and drying the solid was found to weigh 10.1 g. Analysis of the clear supernatant by GC, GC-MS, and 19F NMR indicated the following major products in the Table below.

| Component | GC Area % |
|---|---|
| CCl2CF3 | 13.5 |
| CF3CCl2C2F5 | 80.9 |
| CCl3CF3 | 3.6 |

The modified aluminum chloride catalyst used in this Example was prepared by substantially in accordance with the method described in Example 1 with the exception that 410 g of CCl3F were added to the AlCl3 over the course of 0.3 h.

EXAMPLE 4

Reaction of CBrF2CClF2 with TFE

A 400 mL "Hastelloy" C shaker tube was charged with aluminum chloride (2 g, 0.015 mole) and 59 g of CHCl2CF3

(40 mL, present as a diluent). The tube was sealed, cooled to −78 C, evacuated, and purged with nitrogen three times. The reactor was then charged with CBrF2CClF2 (22 g, 0.10 mole). The cold reactor was placed in the barricade and charged with 15 g (0.15 mole) of TFE, warmed to 80 C, and held at that temperature for 6 h. The pressure quickly rose to 163 psig and then fell off to 89 psig at the end of the reaction period. The following day the reactor was discharged to afford 73.7 g of a yellow supernatant over a dark solid (75% recovery). Analysis of the product by GC and GC-MS indicated the composition given in the table below.

| Component | GC Area % |
| --- | --- |
| C2HF5 | 0.4 |
| C2BrF5 | 0.2 |
| C4ClF7 | 0.4 |
| C2BrClF4 | 2.9 |
| CHCl2CF3 | 68.6 |
| CF3BrClCF2CF3 | 19.6 |
| CBrCl2CF3 | 2.3 |
| CBr2ClCF3 | 0.3 |
| CCl2=CCl2 | 1.6 |
| C5BrClF10 | 0.4 |

The identity of the major products was confirmed by the 19F NMR spectrum of a distillation cut in which the C4BrClF8 component concentration was about 79%.

EXAMPLE 5

Reaction of CBrF2CBrF2 with TFE

A 400 mL "Hastelloy" C shaker tube was charged with 3 g of CCl3F-modified aluminum chloride (E65330-70). The reactor was sealed, cooled to −78 C, evacuated, and charged with 50 g (0.19 mole) of CBrF2CBrF2. The reactor was purged with nitrogen three times, placed in the autoclave, and agitated. 21 g (0.21 mole) of TFE added and the reactor was heated to 100 C. The temperature was held at 99–100 C for 4 h; the pressure in the reactor gradually increased to 40 psig. Upon opening the reactor, 70.4 g (95% recovery) of product were obtained which consisted of an amber liquid over a dark solid. Analysis of the product by GC and GC-MS indicated the following major prodcucts in the Table below. The 19F NMR spectrum of the product verified the presence of CF3CBr2CF2CF3; and excluded the possibility of CBrF2CBrFCF2CF3 as a major product; nine additional minor impurities were observed, but not identified.

| Component | GC Area % |
| --- | --- |
| C4F8 | 0.5 |
| C6F12 | 1.5 |
| C8F16 | 0.2 |
| C4BrF9 | 0.1 |
| C4BrF7 isomer | 0.2 |
| C4BrF7 isomer | 0.3 |
| C6BrF11 isomer | 2.3 |
| C6BrF11 isomer | 0.6 |
| C6BrF11 isomer | 0.8 |
| C6BrF11 isomer | 0.4 |
| C8BrF15 isomer | 0.7 |
| C8BrF15 isomer | 0.4 |
| CF3CBr2CF2CF3 | 89.1 |
| C6BrClF10 | 0.2 |
| C8BrClF14 | 0.2 |

The modified aluminum chloride catalyst used in Example 5 was prepared by a procedure similar to that described in Example 2. Analysis: weight % Al=27.7; this corresponds to a composition that is approximately AlCl0.8F2.2.

Without wishing to be bound by any theory or explanation, it is believed that the starting material is being isomerized under the reaction conditions to an intermediate product, e.g., CF3CBr2F, that in turn reacts with TFE to form a reaction product comprising CF3CBr2CF2CF3. This Example demonstrates that a perhalofluoroethane having a CF2XCF2X structure reacts with a fluoroolefin, e.g., TFE, to form a CF3CX2CF2CF3 structure, where X can be Cl and/or Br such that at least one X is Br.

EXAMPLE 6

Reaction of CBrF2CBrF2 with TFE in the presence of AlCl3

A 400 mL "Hastelloy" C shaker tube was charged with 2 g (0.015 mole) of aluminum chloride and 120 g (0.46 mole) of CBrF2CBrF2. The reactor was cooled, evacuated, purged with nitrogen three times, placed in the autoclave, and agitated. TFE (10 g, 0.10 mole) were added to the reactor was heated to 103 C over the course of 0.25 h. An exotherm occurred at this point which resulted in a decrease in pressure from 50 to 35 psig. An additional 40 g of TFE were added over the next 0.5 h in such a way that the pressure did not exceed 150 psig. The temperature was held overnight at 99–100 C. Upon discharge, 151.8 g of product were obtained which consisted of a yellow-orange supernatant over a dark solid. Analysis of the product by GC and GC-MS indicated the following major products:

| Compound | GC Area % |
| --- | --- |
| C4BrClF8 | 2.9 |
| CF3CBr2C2F5 | 82.9 |
| C2Br2ClF3 | 1.3 |
| C2Br3F3 | 5.2 |

EXAMPLE 7

Reaction of CBr2FCF3 with TFE

Following a procedure similar to that above, a 400 mL "Hastelloy" C reactor was charged with CBr2FCF3 (50 g, 0.19 mole), CCl3F-modified aluminum chloride (2 g; see Example 2), and TFE (21 g, 0.21 mole). The reactor heated at 74–95C for 6 h; the pressure changed from 55 psig to 44 psig during this time. The product (66.3 g) consisted of a yellow supernatant over a tan solid. GC/GC-MS analysis indicated that the product was 96% CF3CBr2C2F5.

EXAMPLE 8

Reaction of CCl2FCClF2 with CTFE

A 400 mL "Hastelloy" C shaker tube was charged with 2 g of CFC-11-modified aluminum chloride (see Example 1). The reactor was sealed, cooled to −78 C, evacuated, purged with nitrogen three times, and charged with 74 g (0.40 mole) of CCl2FCClF2 and 23 g (0.20 mole) of TFE. The reactor was then placed in the autoclave, agitated, and heated to 48 C over the course of about 0.5 h (pressure reached 30 psig). The temperature was adjusted to 39–40 C and held for 6 h; the final pressure was 20 psig. The product consisted of clear supernatant over a brown solid (total weight 91.8 g). Analysis of the product by GC and GC-MS indicated the following major products:

| Component | GC Area % |
|---|---|
| CClF=CF2 | 5.0 |
| cyclo-CC1FCC1FCF2CF2- | 5.3 |
| CC12FCC1F2 | 46.0 |
| CC13CC1F2 | 0.2 |
| C4C14F6 | 42.7 |
| C4C15F5 | 0.6 |

The product was washed twice with water and the organic layer placed in a distillation flask connected to a seven inch 12 mm i.d. vacuum-jacketed column packed with ¼ inch glass helices and topped with a water-cooled cold finger head. The product was distilled at atmospheric pressure and three fractions collected. The composition of the first fraction (head temp ambient –48 C) and the third fraction (head temperature 130–133 C) were determined by 19F NMR (see below).

19 F NMR Analysis of Distillation Fractions

|  | Mole Percent | |
|---|---|---|
| Component | Fraction 1 | Fraction 3 |
| cyclo-CC1FCC1FCF2CF2cis isomer | 2.3 | 0.1 |
| bans isomer | 1.8 | 0.1 |
| CC12FCC1F2 | 80.8 | 0.4 |
| CC13CF3 | 15.1 | 0.04 |
| CC1F2CC12CF2CC1F2 | 46.7 | |
| CC1F2CC12CC1FCF3 | 44.5 | |
| CF3CC12CC12CF3 | 4.5 | |
| CC1F2CC1FCC12CF3 | 3.7 | |

EXAMPLE 9

Reaction of CCl2FCF3 with CTFE

A 400 mL "Hastelloy" C shaker tube was charged with 2 g of CCl3F-modified aluminum chloride (Example 1) and 25 g (0.16 mole) of CHCl2CF3. The reactor was sealed, cooled to –78 C, evacuated, purged with nitrogen three times, and charged with 34 g (0.20 mole) of CCl2FCF3 and 23 g (0.20 mole) of CTFE. The reactor was then placed in the autoclave, agitated, and heated to 50–51 C over the course of about 1 h (pressure reached 65 psig). The temperature was held at 50–51 C and held for 4 h; the final pressure was 75 psig. The product consisted of clear supernatant over a dark solid (total weight 61.1 g). Analysis of the product by GC, GC-MS, and 19F NMR indicated the following major products:

| Component | GC Area % | Mole % |
|---|---|---|
| CF3CC12F | 3.4 | 6.4 |
| CC1F2CC1F2 | * | 0.5 |
| CHC12CF3 | 38.0 | 54.6 |
| cyclo-C4C12F6 | 27.4 | 17.4 |
| CC13CF3 | 0.3 | |
| CC1F2CF2CC12CF3 | 29.8 | 10.9 |
| CF3CC12CC1FCF3 | * | 10.2 |
| CC1F2CF2CC13 | 0.7 | |

*Not separated from its isomer on the GC column utilized.

EXAMPLE 10

Hydrogenation of CF3CF2CBr2CF3 over Pd/Al2O3 Catalyst

A 15 inch (38.1 cm) by ⅜ inch (0.95 cm) "Hastelloy" nickel alloy tube is filled with about 3.48 gm (about 6.0 cc) of about 0.5% Pd/Al2O3 (Calsicat ⅛" pellets #64A-057) ground to 4/10 mesh.

The catalyst is activated by heating at about 100 C for about 50 min. under a hydrogen flow of about 50 sccm (8.3×10−7 m3/s). The temperature of the reaction is raised to about 150 C while decreasing the flow of H2 to about 20 sccm (3.3×10−7 m3/s) and increasing the flow of CF3CF2CBr2CF3 to about 10.0 sccm (1.7×10−7 m3/s). The gaseous effluent is CF3CF2CH2CF3.

While certain aspects of the invention have been described in particular detail, a person having ordinary skill in this art will recognized that other aspects and embodiments are encompassed by the appended claims.

What is claimed is:

1. A perhalofluorobutane or perhalofluorohexane product made by a process which comprises:
   (i) contacting
      a) CYF=CF$_2$, wherein Y is Cl or F, with
      b) a perhalofluoroethane selected from the group consisting of CX$_2$FCX$_2$F, CX$_2$FCFXF$_2$, CF$_3$CX$_2$F, and CBrF$_2$CF$_2$X, wherein X is either Cl or Br, in the presence of
      c) a catalytically effective polyvalent metal halide at a temperature and pressure and for a time effective to produce
      d) a reaction product mixture containing at least one perhalofluorobutane selected from the group consisting of C$_4$YX$_4$F$_5$, C$_4$YX$_3$F$_6$, C$_4$BrYXF$_7$, and C$_4$YX$_2$F$_7$, or perhalofluorohexane selected from the group consisting of C$_6$X$_4$Y$_2$F$_8$ and C$_6$ClX$_4$Y$_2$F$_7$ wherein X is as defined above; and
   (ii) recovering at least one of said perhalofluorobutanes or perhalofluorohexanes from the reaction mixture.

2. The product of claim 1 comprising at least one member from the group consisting of C$_2$Cl$_5$C$_2$F$_5$, CF$_3$CCl$_2$CF$_2$CClF$_2$, CF$_3$CBrClC$_2$F$_5$, CF$_3$CBr$_2$C$_2$F$_5$, CClF$_2$CF$_2$CCl$_2$CCl$_2$C$_2$F$_5$ and C$_2$F$_5$CCl$_2$CCl$_2$C$_2$F$_5$.

3. The product of claim 1 wherein said contacting is performed by using tetrafluoroethylene and at least one member from the group consisting of CCl$_2$FCCL$_2$F, CCl$_2$FCClF$_2$, CCl$_2$FCF$_3$, CBrF$_2$CClF$_2$, CBrF$_2$CBrF$_2$, and CBr$_2$FCF$_3$.

* * * * *